United States Patent [19]
Beckmann et al.

[11] Patent Number: 5,696,243
[45] Date of Patent: Dec. 9, 1997

[54] DIPHENYLAMINE COMPOUNDS, POLYMERS PREPARED THEREFROM AND NON-LINEAR OPTICS DEVICES CONTAINING THE SAME

[75] Inventors: Stefan Beckmann, Mannheim; Karl-Heinz Etzbach, Frankenthal; Ruediger Sens, Mannheim, all of Germany

[73] Assignee: GASF Aktiengesellschaft, Ludwigshafen, Germany

[21] Appl. No.: 628,641

[22] PCT Filed: Oct. 10, 1994

[86] PCT No.: PCT/EP94/03330

§ 371 Date: Apr. 19, 1996

§ 102(e) Date: Apr. 19, 1996

[87] PCT Pub. No.: WO95/11278

PCT Pub. Date: Apr. 27, 1995

[30] Foreign Application Priority Data

Oct. 19, 1993 [DE] Germany .................. 43 35 496.3

[51] Int. Cl.[6] .............. C09B 29/033; C09B 29/048; C09B 29/042; C07C 245/08; C07C 255/00; C08F 4/04

[52] U.S. Cl. .............. 534/753; 252/582; 526/218; 534/752; 534/795; 534/829; 534/852; 534/860; 558/401

[58] Field of Search ............. 534/752, 753, 534/852, 860, 795, 829; 526/218, 1; 558/401; 252/582

[56] References Cited

U.S. PATENT DOCUMENTS

| | | | |
|---|---|---|---|
| 3,507,850 | 4/1970 | Cohen et al. | 534/643 |
| 4,843,153 | 6/1989 | Eilingsfeld et al. | 534/752 |
| 5,334,710 | 8/1994 | Ahlheim et al. | 534/852 |

FOREIGN PATENT DOCUMENTS

| | | | |
|---|---|---|---|
| 0 201 896 | 11/1986 | European Pat. Off. | 534/752 |
| 0312856 | 4/1989 | European Pat. Off. | 534/852 |
| 0535490 | 4/1993 | European Pat. Off. | 534/852 |
| 31 08 077 | 1/1982 | Germany | 534/752 |
| 42 13 155 | 11/1992 | Germany | 534/752 |
| 1223441 | 2/1971 | United Kingdom | 534/852 |
| 1 546 803 | 5/1979 | United Kingdom | 534/752 |
| 2255336 | 4/1992 | United Kingdom | 534/852 |

OTHER PUBLICATIONS

Angew. Chem., vol. 96, 1984, pp. 637–651, David J. Williams, "Organische Polymere Und Nichtpolymere Materialien Mit Guten Nichtlinearen Optischen Eigenschaften".

J. Chem. Soc., pp. 103–116, 1942, J. N. Ashley, et al., "A Chemotherapeutic Comparison of the Trypanocidal Action of Some Aromatic Diamidines".

J. Am. Chem. Soc., vol. 80, pp. 2815–2822, 1958, G. N. Sausen, et al., "Cyanocarbon Chemistry. VII. Tricyanoethylenes".

Journal of Polymer Science: Part A: Polymer Chemistry, vol. 28, pp. 1–13, 1990, Douglas R. Robello, "Linear Polymers For Nonlinear Optics I. Polyacrylates Bearing Aminonitro-Stilbene and -Azobenzene Dyes".

Z. Naturforschg., vol. 20a, pp. 1441–1471, 1965, W. Liptay, "Die Loesungsmittelabhaengigkeit Der Wellenzahl Von Elektronenbanden Und Die Chemisch–Physikalischen Grundlagen".

J. Org. Chem., vol. 54, 1989, pp. 3774–3778, M.S. Paley, et al., "A Solvatochromic Method for Determining Second-Order Polarizabilities of Organic Molecules".

Chemistry & Industry, Oct. 1, 1990, pp. 600–608, Carole Jones, "Polymers for Non–Linear Optical Devices".

11th International Colour Symposium, Manuscripts and Abstracts, Sep. 23–26, 1991, M. G. Hutchings, et al., "Application of Dyes in Nonlinear Optical Materials".

*Primary Examiner*—Floyd D. Higel
*Attorney, Agent, or Firm*—Oblon, Spivak, McClelland, Maier & Neustadt, P.C.

[57] ABSTRACT

Diphenylamines of the formula

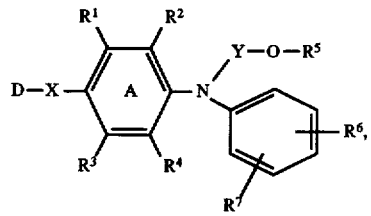

where the ring A can be benzo-fused, and

D is aryl or a five-membered aromatic heterocyclyl which contains one to three hetero atoms selected from the group consisting of nitrogen, oxygen and sulfur, in the heterocyclic ring and can be fused to a benzene, thiophene, pyridine or pyrimidine ring, X is $N=N$ or, if D is aryl, is alternatively $CH=CH$, or D—X together is 1,2,2-tricyanovinyl, $R^1$, $R^2$, $R^3$ and $R^4$ are each hydrogen, $C_1$–$C_6$-alkyl, $C_1$–$C_6$-alkoxy or halogen, $R^5$ is prop-1-en-3-yl, acryloyl or methacryloyl, $R^6$ and $R^7$ are each hydrogen, $C_1$–$C_6$-alkyl, $C_1$–$C_6$-alkoxy, halogen, prop-1-en-3-yl, acryloyl, methacryloyl or oxiranylmethoxy, and Y is $C_1$–$C_{20}$-alkylene, polymers derived from the compounds, and their use in non-linear optics.

8 Claims, No Drawings

DIPHENYLAMINE COMPOUNDS, POLYMERS PREPARED THEREFROM AND NON-LINEAR OPTICS DEVICES CONTAINING THE SAME

The present invention relates to novel diphenylamines of the formula I

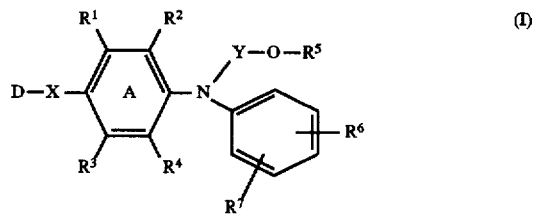

(I)

where the ring A can be benzo-fused, and

D is aryl or a five-membered aromatic heterocyclyl which contains one to three hetero atoms selected from the group consisting of nitrogen, oxygen and sulfur, in the heterocyclic ring and can be fused to a benzene, thiophene, pyridine or pyrimidine ring, X is N=N or, if D is aryl, is alternatively CH=CH, or D—X together is 1,2,2-tricyanovinyl, $R^1$, $R^2$, $R^3$ and $R^4$, independently of one another, are each hydrogen, $C_1$–$C_6$-alkyl, $C_1$–$C_6$-alkoxy or halogen, $R^5$ is prop-1-en-3-yl, acryloyl or methacryloyl, $R^6$ and $R^7$, independently of one another, are each hydrogen, $C_1$–$C_6$-alkyl, $C_1$–$C_6$-alkoxy, halogen, prop-1-en-3-yl, acryloyl, methacryloyl or oxiranylmethoxy, and Y is $C_1$–$C_{20}$-alkylene, to polymers derived from the novel compounds, and to their use in nonlinear optics.

DE-A-4 213 155 describes azo dyes having a diazo component from the aniline series and a coupling component from the N-benzyl- or N-phenylethylaniline series, homopolymers or copolymers thereof, and their use in nonlinear optics.

Furthermore, Angew. Chem., 96 (1984), 637 to 651, discloses the use of stilbene derivatives or specific azo dyes for this purpose.

It is an object of the present invention to provide novel compounds based on stilbene derivatives, tricyanovinylbenzenes and aryl- or hetarylazobenzenes or -naphthalenes which are advantageously suitable for use in nonlinear optical systems. In particular, these compounds should have high hyperpolarizability values and should be stable to heat and oxidation. The compounds should also be polymerizable, and the systems obtained from them should have a high glass transition temperature.

We have found that this object is achieved by the diphenylamines of the formula I described in greater detail in the introduction.

Preference is given to diphenylamines of the formula I in which D is aryl or heterocyclyl selected from the series consisting of pyrrolyl, furanyl, thiophenyl, pyrazolyl, imidazolyl, oxazolyl, isoxazolyl, thiazolyl, isothiazolyl, triazolyl, oxadiazolyl, thiadiazolyl, benzofuranyl, benzothiophenyl, benzimidazolyl, benzoxazolyl, benzothiazolyl, benzisothiazolyl, pyridothiophenyl, pyrimidothiophenyl and thienothiazolyl.

Particular preference is given to diphenylamines of the formula I in which D is aryl or heterocyclyl from the series consisting of pyrrolyl, thiophenyl, pyrazolyl, thiazolyl, isothiazolyl, triazolyl, thiadiazolyl, benzothiophenyl, benzothiazolyl, benzisothiazolyl, pyridothiophenyl, pyrimidothiophenyl and thienothiazolyl.

Particular importance is attached to diphenylamines of the formula I in which

D is

(IIa)

(IIb)

(IIc)

(IId)

(IIe)

(IIf)

(IIg)

(IIh)

(IIi)

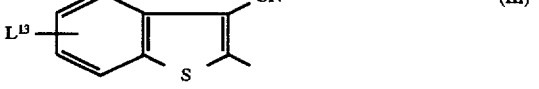
(IIj)

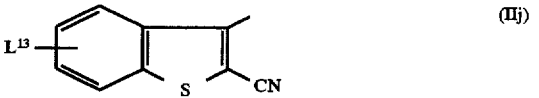
(IIk)

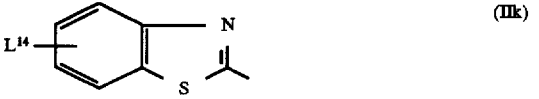
(III)

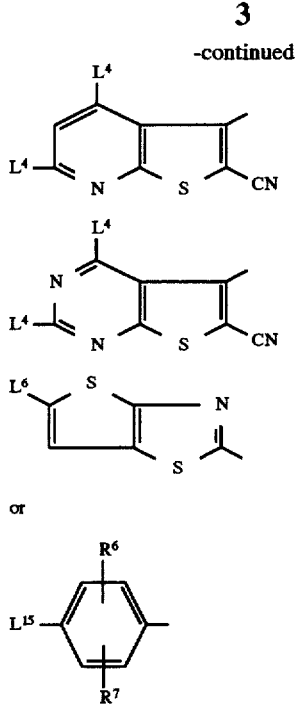

where
- $L^1$ is nitro, cyano, $C_1$–$C_6$-alkanoyl, benzoyl, $C_1$–$C_6$-alkylsulfonyl, substituted or unsubstituted phenylsulfonyl or —CH=T, where T is hydroxyimino, $C_1$–$C_4$-alkoxyimino or a radical of a CH-acidic compound,
- $L^2$ is hydrogen, $C_1$–$C_6$-alkyl, halogen, hydroxyl, mercapto, unsubstituted or phenyl- or $C_1$–$C_4$-alkoxy-substituted $C_1$–$C_6$-alkoxy, unsubstituted or substituted phenoxy, unsubstituted or phenyl-substituted $C_1$–$C_6$-alkylthio, unsubstituted or substituted phenylthio, $C_1$–$C_6$-alkylsulfonyl or unsubstituted or substituted phenylsulfonyl,
- $L^3$ is cyano, $C_1$–$C_4$-alkoxycarbonyl or nitro,
- $L^4$ is hydrogen, $C_1$–$C_6$-alkyl or phenyl,
- $L^5$ is $C_1$–$C_6$-alkyl or phenyl,
- $L^6$ is hydrogen, cyano, $C_1$–$C_4$-alkoxycarbonyl, $C_1$–$C_6$-alkanoyl, thiocyanato or halogen,
- $L^7$ is nitro, cyano, $C_1$–$C_6$-alkanoyl, benzoyl, $C_1$–$C_4$-alkoxycarbonyl, $C_1$–$C_6$alkylsulfonyl, substituted or unsubstituted phenylsulfonyl or —CH=T, where T is as defined above,
- $L^8$ is hydrogen, $C_1$–$C_6$-alkyl, cyano, halogen, unsubstituted or phenyl- or $C_1$–$C_4$-alkoxy-substituted $C_1$–$C_6$-alkoxy, unsubstituted or phenyl-substituted $C_1$–$C_6$-alkylthio, unsubstituted or substituted phenylthio, $C_1$–$C_6$-alkylsulfonyl, unsubstituted or substituted phenylsulfonyl or $C_1$–$C_4$-alkoxycarbonyl,
- $L^9$ is cyano, unsubstituted or phenyl-substituted $C_1$–$C_6$-alkyl, unsubstituted or phenyl-substituted $C_1$–$C_6$-alkylthio, unsubstituted or substituted phenyl, thienyl, $C_1$–$C_4$-alkylthienyl, pyridyl or $C_1$–$C_4$-alkylpyridyl,
- $L^{10}$ is phenyl or pyridyl,
- $L^{11}$ is trifluoromethyl, nitro, $C_1$–$C_6$-alkyl, phenyl, unsubstituted or phenyl-substituted $C_1$–$C_6$-alkylthio or $C_1$–$C_6$-dialkylamino,
- $L^{12}$ is $C_1$–$C_6$-alkyl, phenyl, 2-cyanoethylthio or 2-($C_1$–$C_4$-alkoxycarbonyl)ethylthio,
- $L^{13}$ is hydrogen, nitro or halogen,
- $L^{14}$ is hydrogen, cyano, $C_1$–$C_4$-alkoxycarbonyl, nitro or halogen, and
- $L^{15}$ is cyano, nitro, hydroxysulfonyl, 2,2-dicyanovinyl, 1,2,2-tricyanovinyl or E—N=N, where E is phenyl which is substituted by cyano, nitro, 2,2-dicyanovinyl or 1,2,2-tricyanovinyl, and
- $R^6$ and $R^7$ are each as defined above.

All the alkyl and alkylene groups which occur in the above formulae I and II may be either straight-chain or branched.

If the above formulae I and II contain any substituted phenyl groups, examples of possible substituents are, unless stated otherwise, $C_1$–$C_4$-alkyl, chlorine, bromine, nitro or $C_1$–$C_4$-alkoxy. The phenyl radicals here generally have from 1 to 3 substituents.

If the above formulae I and II contain any substituted alkyl groups, these generally have 1 or 2 substituents.

$L^2, L^4, L^5, L^8, L^9, L^{11}, L^{12}, R^1, R^2, R^3, R^4, R^6$ and $R^7$ are, for example, methyl, ethyl, propyl, isopropyl, butyl, isobutyl, sec-butyl, pentyl, isopentyl, neopentyl, tert-pentyl, hexyl or 2-methylpentyl.

$L^9$ may additionally be, for example, benzyl or 1- or 2-phenylethyl.

$L^2$, $L^8$, $L^9$ and $L^{11}$ may additionally be, for example, methylthio, ethylthio, propylthio, isopropylthio, butylthio, isobutylthio, pentylthio, hexylthio, benzylthio or 1- or 2-phenylethylthio.

$L^2$ and $L^8$ may additionally be, for example, phenylthio, 2-methyl-phenylthio, 2-methoxyphenylthio or 2-chlorophenylthio.

$L^2, L^8, R^1, R^2, R^3, R^4, R^6$ and $R^7$ may additionally be, for example, methoxy, ethoxy, propoxy, isopropoxy, butoxy, isobutoxy, sec-butoxy, pentoxy, isopentoxy, neopentoxy, tert-pentoxy, hexyloxy or 2-methylpentoxy.

$L^6, L^2, L^8, L^{13}, L^{14}, R^1, R^2, R^3, R^4, R^6$ and $R^7$ can be, for example, fluorine, chlorine or bromine.

$L^7, L^1, L^2$ and $L^8$ can be, for example, methylsulfonyl, ethylsulfonyl, propylsulfonyl, isopropylsulfonyl, butylsulfonyl, isobutylsulfonyl, sec-butylsulfonyl, pentylsulfonyl, isopentylsulfonyl, neopentylsulfonyl, hexylsulfonyl, phenylsulfonyl, 2-methylphenylsulfonyl, 2-methoxyphenylsulfonyl or 2-chlorophenylsulfonyl.

$L^3, L^6, L^7, L^8$ and $L^{14}$ can be, for example, methoxycarbonyl, ethoxycarbonyl, propoxycarbonyl, isopropoxycarbonyl, butoxycarbonyl, isobutoxycarbonyl or sec-butoxycarbonyl.

$L^2$ and $L^8$ can additionally be, for example, 2-methoxyethoxy, 2-ethoxyethoxy, 2- or 3-methoxypropoxy, 2- or 3-ethoxypropoxy, 2- or 4-methoxybutoxy, 2- or 4-ethoxybutoxy, 5-methoxypentoxy, 5-ethoxypentoxy, 6-methoxyhexyloxy, 6-ethoxyhexyloxy, benzyloxy or 1- or 2-phenylethoxy.

$L^{11}$ can additionally be, for example, dimethylamino, diethylamino, dipropylamino, diisopropylamino, dibutylamino, dipentylamino, di-hexylamino or N-methyl-N-ethylamino.

$L^{12}$ can additionally be, for example, 2-methoxycarbonylethylthio or 2-ethoxycarbonylethylthio.

$L^9$ can additionally be, for example, phenyl, 2-, 3- or 4-methylphenyl, 2,4-dimethylphenyl, 2-, 3- or 4-methoxyphenyl, 2,4-dimethoxyphenyl, 2-, 3- or 4-chlorophenyl, 2-, 3- or 4-methoxyphenyl, 2- or 3-methylthienyl or 2-, 3- or 4-methylpyridyl.

$L^1, L^6$ and $L^7$ can additionally be, for example, formyl, acetyl, propionyl, butyryl, pentanoyl or hexanoyl.

If $L^1$ or $L^7$ is —CH=T where T is derived from a CH-acidic compound $H_2T$, the CH-acidic compound $H_2T$ can be, for example, a compound of the formula

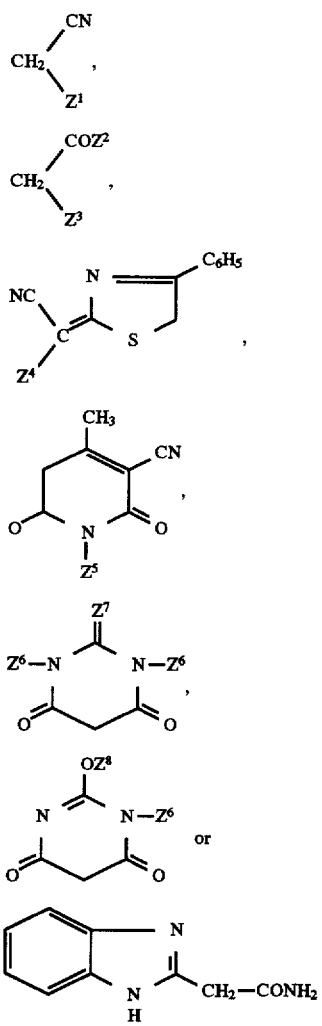

(IIIa)

(IIIb)

(IIIc)

(IIId)

(IIIe)

(IIIf)

or (IIIg)

where $Z^1$ is cyano, nitro, $C_1$–$C_4$-alkanoyl, unsubstituted or substituted benzoyl, $C_1$–$C_4$-alkylsulfonyl, unsubstituted or substituted phenylsulfonyl, carboxyl, $C_1$–$C_4$-alkoxycarbonyl, $C_3$–$C_4$-alkenyloxycarbonyl, phenoxycarbonyl, carbamoyl, $C_1$–$C_4$-mono- or dialkylcarbamoyl, unsubstituted or substituted phenylcarbamoyl, unsubstituted or substituted phenyl, benzothiazol-2-yl, benzimidazol-2-yl, 5-phenyl-1,3,4-thiadiazol-2-yl or 2-hydroxyquinoxalin-3-yl, $Z^2$ is $C_1$–$C_4$-alkyl, $C_1$–$C_4$-alkoxy or $C_3$–$C_4$-alkenyloxy, $Z^3$ is $C_1$–$C_4$-alkoxycarbonyl, $C_3$–$C_4$-alkenyloxycarbonyl, phenylcarbamoyl or benzimidazol-2-yl, $Z^4$ is cyano, $C_1$–$C_4$-alkoxycarbonyl or $C_3$–$C_4$-alkenyloxycarbonyl, $Z^5$ is hydrogen, $C_1$–$C_6$-alkyl, $C_1$–$C_4$-alkenylamino or benzoylamino, $Z^6$ is hydrogen, $C_1$–$C_4$-alkyl or phenyl, $Z^7$ is oxygen or sulfur, and $Z^8$ is $C_1$–$C_4$-alkyl.

Special mention should be made here of the radical derived from compounds of the formula IIIa, IIIb or IIIc in which $Z^1$ is cyano, $C_1$–$C_4$-alkanoyl, $C_1$–$C_4$-alkoxycarbonyl or $C_3$–$C_4$-alkenyloxycarbonyl, $Z^2$ is $C_1$–$C_4$-alkyl, $C_1$–$C_4$-alkoxy or $C_3$–$C_4$-alkenyloxy, $Z^3$ is $C_1$–$C_4$-alkoxycarbonyl or $C_3$–$C_4$-alkenyloxycarbonyl, and $Z^4$ is cyano.

Very particular mention should be made here of the radical derived from compounds of the formula IIIa, IIIb or IIIc in which $Z^1$ is cyano, $C_1$–$C_4$-alkoxycarbonyl or $C_3$–$C_4$-alkenyloxycarbonyl, $Z^2$ is $C_1$–$C_4$-alkoxy or $C_2$–$C_4$-alkenyloxy, $Z^3$ is $C_1$–$C_4$-alkoxycarbonyl or $C_3$–$C_4$-alkenyloxycarbonyl, and $Z^4$ is cyano.

$L^{15}$ is, for example, 2- or 4-cyanophenyl, 2- or 4-nitrophenyl, 2- or 4-hydroxysulfonylphenyl, 2- or 4-(2,2-dicyanovinyl)phenyl or 2- or 4-(1,2,2-tricyanovinyl)phenyl.

Y is, for example, $CH_2$, $(CH_2)_2$, $(CH_2)_3$, $(CH_2)_4$, $(CH_2)_5$, $(CH_2)_6$, $(CH_2)_7$, $(CH_2)_8$, $(CH_2)_9$, $(CH_2)_{10}$, $CH(CH_3)CH_2$ or $CH(CH_3)CH(CH_3)$.

Particular mention should be made of diphenylamines of the formula I in which D is aryl, thienyl, thiazolyl or thiadiazolyl, where particular mention should be made of radicals of the formulae IIb, IId, IIg and IIp.

Particular mention should furthermore be made of diphenylamines of the formula I in which X is N=N.

Particular mention should furthermore be made of diphenylamines of the formula I in which $R^1$, $R^2$, $R^3$ and $R^4$ are each hydrogen.

Particular mention should furthermore be made of diphenylamines of the formula I in which $R^6$ and $R^7$ are each hydrogen.

Particular mention should furthermore be made of diphenylamines of the formula I in which $R^5$ is acryloyl or methacryloyl.

Particular mention should furthermore be made of diphenylamines of the formula I in which Y is $C_2$–$C_6$-alkylene.

The diphenylamines of the formula I can be prepared by methods known per se.

Compounds of the formula I in which X is N=N can be obtained, for example, by the methods described in EP 201 896, DE-A 3 108 077, U.S. Pat. No. 4,843,153 or GB-A 1,546,803. For example, an amine of the formula IV

where D is as defined above, can be diazotized and coupled to a coupling component of the formula V

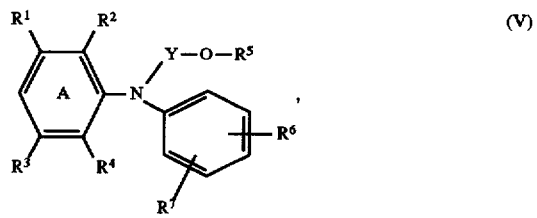

where the ring A, $R^1$, $R^2$, $R^3$, $R^4$, $R^5$, $R^6$, $R^7$ and Y are each as defined above.

The compounds of the formula I in which X is CH=CH can be obtained, for example, by the method described in J. Chem. Soc., 1942, 103 to 116. For example, aromatic aldehydes can be reacted with phosphorus ylides in a Wittig-type reaction.

The compounds of the formula I in which D—X together are 1,2,2-tricyanovinyl can be obtained, for example, by the method described in J. Am. Chem. Soc., 80 (1958), 2815 to 2822.

The present invention furthermore relates to diphenylamine-containing polymers which contain, as characteristic monomer units, a divalent radical derived from a diphenylamine of the formula I, and radicals of the formulae VI, VII and VIII

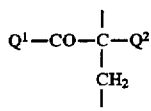  (VI)

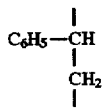  (VII)

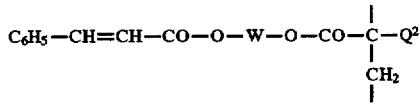  (VIII)

where $Q^1$ is hydroxyl, $C_1$-$C_6$-alkoxy, oxiranylmethoxy, phenoxy, amino or $C_1$-$C_4$-mono- or dialkylamino, $Q^2$ is hydrogen or methyl, and W is $C_2$-$C_{10}$-alkylene, where the proportion of monomer units of divalent radicals derived from the formula I is from 1 to 100 mol %, that of the formula VI is from 0 to 99 mol %, that of the formula VII is from to 99 mol % and that of the formula VIII is from 0 to 75 mol %, in each case based on the polymer, and the mean molecular weight of the polymer is from 1,000 to 500,000.

One divalent radical derived from a diphenylamine of the formula I preferably conforms to the formula Ia or Ib

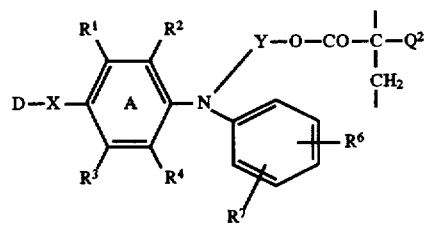  (Ia)

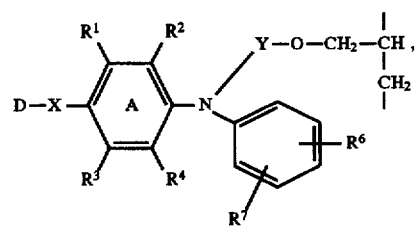  (Ib)

The novel polymers can be prepared by methods known per se, as described, for example, in J. Polymer Sci., Part A, Polymer Chem., 28 (1990), 1 to 13.

In an expedient reaction, a corresponding diphenylamine of the formula I is reacted with an acrylic compound of the formula IX

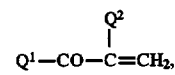  (IX)

where $Q^1$ and $Q^2$ are each as defined above, styrene and a cinnamic ester of the formula X

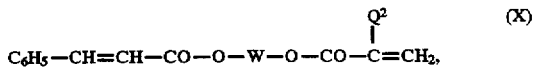  (X)

where $Q^2$ and W are each as defined above, in the above molar ratio in an inert solvent (for example toluene or xylene) in the presence of a free-radical initiator (for example azobisisobutyronitrile).

The diphenylamines of the formula I and the polymers containing diphenylamines of the formula I are advantageously suitable for use in nonlinear optics.

The novel compounds are stable to oxidation and have particularly large molecular hyperpolarizability values (β). In addition, the polymers have a high glass transition temperature and thus high relaxation stability.

The molecular hyperpolarizability can be determined, for example, by the solvatochromism method (see, for example, Z. Naturforschung 20a (1965), 1441 to 1471, or J. Org. Chem., 54 (1989), 3775 to 3778), in which the position of the absorption band of a compound is determined in various solvents. The shift of the absorption band is then directly proportional to the β value, i.e. compounds having a large solvatochromic shift have large molecular hyperpolarizability and are therefore highly suitable for use in nonlinear optical systems (see, for example, Chemistry and Industry (1990), 600 to 608).

Particular mention should be made here of the suitability of the novel substances in communications technology, electrooptical modulators (e.g. Mach-Zehnder interferometer), optical switches, frequency mixing or waveguides.

The examples below illustrate the invention in greater detail.

EXAMPLE 1 a) 169.1 g (1 mol) of diphenylamine and 6.76 g (49 mmol) of anhydrous zinc chloride were introduced into a 0.5 l autoclave, and 46.2 g (1.05 mol) of ethylene oxide were subsequently injected at 110° C. under nitrogen pressure (maximum pressure 6 atm.). The mixture was then stirred at 110° C. for 3 hours. When the reaction was complete, the reaction product was distilled under reduced pressure, giving 185.3 g (87%) of a pale yellow oil of the formula $(C_6H_5)_2NC_2H_4OH$.

b) 63.9 g (0.3 mol) of the product described under a) were introduced into 600 ml of methylene chloride and 60 ml of triethylamine. 62.2 g (0.35 mol) of methacryloyl chloride, 40 dissolved in 150 ml of methylene chloride, were added dropwise, and the mixture was stirred at room temperature for a further 48 hours. The reaction solution was then extracted twice with saturated sodium hydrogencarbonate solution, dried over sodium sulfate and evaporated under reduced pressure, 45 giving 69 g (88.1%) of a pale oil of the formula

c) 10 g (0.04 mol) of 4-amino-4'-nitroazobenzene were diazotized by means of nitrosylsulfuric acid in 300 ml of 85% strength sulfuric acid. 11.2 g (0.04 mol) of the product described under b) in 100 g of ice, 30 ml of conc. hydrochloric acid and 80 ml of N,N-dimethylformamide (DMF) were added at 0° C. to this solution. After 1 hour, the pH was adjusted to 4 by means of sodium acetate, and the mixture was stirred for a further 48 hours. The resultant dye was subsequently filtered off with suction, washed with water and dried under reduced pressure, giving 6.2 g of the dye of the formula

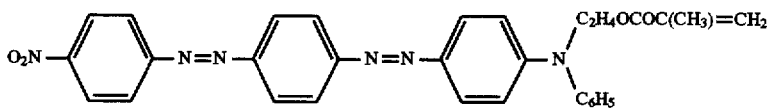

(10)

EXAMPLE 2

6.5 g (0.04 mol) of 3,5-dicyano-4-methyl-2-aminothiophene were diazotized at −5° C. by means of nitrosylsulfuric acid in 300 ml of 85% strength sulfuric acid. This solution was added at −5° C. to a solution of 11.2 g (0.04 mol) of the product described in Example 1b) in 100 g of ice, 30 ml of conc. hydrochloric acid and 80 ml of DMF. After about 1 hour, the pH was adjusted to 4 by means of sodium acetate. After a further 24 hours, the dye was filtered off with suction, washed with water and dried under reduced pressure, giving 5.8 g of a dye of the formula

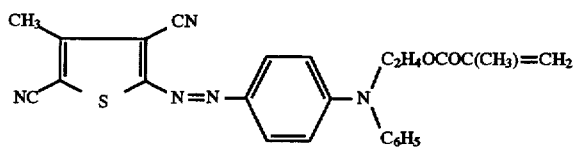

EXAMPLE 3

0.04 mol of 4-nitroaniline were diazotized at 0° C. by means of nitrosylsulfuric acid in 300 ml of 85% strength sulfuric acid. The diazo solution was added at 0° C. to a solution of 11.2 g (0.04 mol) of N-(6-methacryloyloxyhexyl)diphenylamine, prepared by a method similar to that of Example 1b, in 100 g of ice, 30 ml of conc. hydrochloric acid and 80 ml of DMF. After about 1 hour, the pH was adjusted to 4 by means of sodium acetate. The mixture was subsequently stirred for a further 24 hours, and the dye was filtered off with suction, washed with water and dried under reduced pressure, giving 8.8 g of a dye of the formula

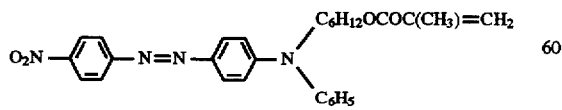

The dyes shown below were obtained similarly.

| Ex. No. | Formula |
|---|---|
| 4 | H₃C—C(=N-S-C(CN))—N=N—C₆H₄—N(C₆H₅)(C₂H₄OCOC(CH₃)=CH₂) |
| 5 | O₂N—C₆H₄—N=N—C₆H₄—N=N—C₆H₄—N(C₆H₅)(C₆H₁₂OCOC(CH₃)=CH₂) |
| 6 | O₂N—C₆H₄—N=N—C₆H₄—N=N—C₆H₄—N(C₆H₅)(C₂H₄OCOCH=CH₂) |
| 7 | CH₃-thiophene(CN)(CN)—N=N—C₆H₄—N(C₆H₅)(C₆H₁₂OCOCH=CH₂) |
| 8 | O₂N—C(N=N)—S—C—N=N—C₆H₄—N(C₆H₅)(C₂H₄OCOCH=CH₂) (thiadiazole) |
| 9 | Cl-thiophene(CN)(CN)—N=N—C₆H₄—N(C₆H₅)(C₄H₈OCOCH=CH₂) |
| 10 | Cl-thiophene(CN)(OHC)—N=N—C₆H₄—N(C₆H₅)(C₂H₄OCOC(CH₃)=CH₂) |
| 11 | (NC)₂C=C(CN)—C₆H₄—N(C₆H₅)(C₂H₄OCOC(CH₃)=CH₂) |
| 12 | O₂N—C₆H₄—N=N—naphthyl—N(C₆H₅)(C₂H₄OCOC(CH₃)=CH₂) |

We claim:
1. A diphenylamine of the formula I

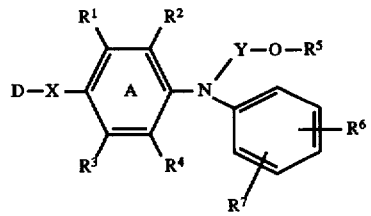

(I)

where the ring A is an unfused or benzo-fused ring, and

D is aryl or a five-membered aromatic heterocyclyl which contains one to three hetero atoms selected from the group consisting of nitrogen, oxygen and sulfur, in the heterocyclic ring or is further fused to a benzene, thiophene, pyridine or pyrimidine ring, X is N=N; or, if D is aryl, X is N=N, or CH=CH; or D—X together is 1,2,2-tricyanovinyl, $R^1$, $R^2$, $R^3$ and $R^4$, independently of one another, are each hydrogen, $C_1$–$C_6$-alkyl, $C_1$–$C_6$-alkoxy, or halogen, $R^5$ is prop-1-en-3-yl, acryloyl, or methacryloyl $R^6$ and $R^7$, independently of one another, are each hydrogen, $C_1$–$C_6$alkyl $C_1$–$C_6$-alkoxy, halogen, prop-1-en-3-yl, acryloyl, methacryloyl or oxiranylmethoxy, and Y is $C_1$–$C_{20}$-alkylene.

2. A diphenylamine as claimed in claim 1, wherein D is aryl or heterocyclyl selected from the group consisting of pyrrolyl, furanyl, thiophenyl, pyrazolyl, imidazolyl, oxazolyl, isoxazolyl, thiazolyl, isothiazolyl, triazolyl, oxadiazolyl, thiadiazolyl, benzofuranyl, benzothiophenyl, benzimidazolyl, benzoxazolyl, benzothiazolyl, benzisothiazolyl, pyridothiophenyl, pyrimidothiophenyl and thienothiazolyl.

3. A diphenylamine as claimed in claim 1, wherein D is aryl or heterocyclyl from the group consisting of pyrrolyl, thiophenyl, pyrazolyl, thiazolyl, isothiazolyl, triazolyl, thiadiazolyl, benzothiophenyl, benzothiazolyl, benzisothiazolyl, pyridothiophenyl, pyrimidothiophenyl and thienothiazolyl.

4. A diphenylamine as claimed in claim 1, wherein X is N=N.

5. A diphenylamine as claimed in claim 1, wherein $R^1$, $R^2$, $R^3$ and $R^4$ are each hydrogen.

6. A diphenylamine as claimed in claim 1, wherein $R^6$ and $R^7$ are each hydrogen.

7. A diphenylamine as claimed in claim 1, wherein $R^5$ is acryloyl or methacryloyl.

8. In a non-linear optics device containing a Compound having molecular hyperpolarizability, the improvement wherein the compound having molecular hyperpolarizability is a diphenylamine compound as claimed in claim 1.

* * * * *

UNITED STATES PATENT AND TRADEMARK OFFICE
CERTIFICATE OF CORRECTION

PATENT NO.  : 5,696,243
DATED       : December 9, 1997
INVENTOR(S) : Stefan BECKMANN et al.

It is certified that error appears in the above-identified patent and that said Letters Patent is hereby corrected as shown below:

On the title page, Item [73], the Assignee should read:

-- BASF Aktiengesellschaft, Ludwigshafen, Germany --

Signed and Sealed this

Twenty-fourth Day of February, 1998

Attest:

BRUCE LEHMAN

Attesting Officer        Commissioner of Patents and Trademarks